United States Patent [19]

Urfer et al.

[11] Patent Number: 5,627,144

[45] Date of Patent: May 6, 1997

[54] COMPOSITION FOR ENHANCED CRUDE OIL RECOVERY OPERATIONS CONTAINING HYDROCHLORIC ACID OR HYDROFLUORIC ACID, OR MIXTURES THEREOF WITH ESTER QUATERNARY AMMONIUM COMPOUNDS OR/AND ALKYL QUATERNARY AMMONIUM COMPOUNDS

[75] Inventors: Allen D. Urfer, Lansdale, Pa.; Oriol P. Obiols, Barcelona; Núria Bonastre, Barberà del Vallès, both of Spain

[73] Assignees: Henkel Kommanditgesellschaft auf Aktien, Duesseldorf, Germany; Pulcra S.A., Barcelona, Spain; Henkel Corporation, Plymouth Meeting, Pa.

[21] Appl. No.: 473,678

[22] Filed: Jun. 7, 1995

Related U.S. Application Data

[62] Division of Ser. No. 943,957, Sep. 11, 1992.

[51] Int. Cl.$^6$ ........................................... C09K 7/00
[52] U.S. Cl. .......................... 507/211; 507/240; 507/269; 510/188
[58] Field of Search ........................... 507/211, 240, 507/269; 510/188

[56] References Cited

U.S. PATENT DOCUMENTS

| H269 | 5/1987 | Malik | 422/37 |
|---|---|---|---|
| 4,259,217 | 3/1981 | Murphy | 252/547 |
| 4,493,773 | 1/1985 | Cook et al. | 252/8.8 |
| 4,606,850 | 8/1986 | Malik | 252/52.8 |
| 4,804,497 | 2/1989 | Urfer et al. | 252/8.8 |
| 5,023,003 | 6/1991 | Yamamura et al. | 252/8.8 |
| 5,024,276 | 6/1991 | Bochardt | 166/308 |
| 5,133,885 | 7/1992 | Contor et al. | 252/8.6 |

FOREIGN PATENT DOCUMENTS

| 0094118 | 11/1983 | European Pat. Off. . |
|---|---|---|
| 0070074 | 6/1988 | European Pat. Off. . |
| 0301298 | 7/1988 | European Pat. Off. . |
| 3702287 | 8/1987 | Germany . |
| 2185992 | 9/1990 | United Kingdom . |
| 8605509 | 9/1986 | WIPO . |
| 8605187 | 9/1986 | WIPO . |
| 8702050 | 4/1987 | WIPO . |

OTHER PUBLICATIONS

"Kosmetische Faerbemittel", Verlag Chemie, Weinheim, 1984, pp. 81–106.

*Primary Examiner*—Sharon Gibson
*Assistant Examiner*—Valerie Fee
*Attorney, Agent, or Firm*—Wayne C. Jaeschke; John E. Drach; Henry E. Millson, Jr.

[57] ABSTRACT

Detergent compositions comprised of an alkyl polyglycoside and an ester quat corresponding to formula (II)

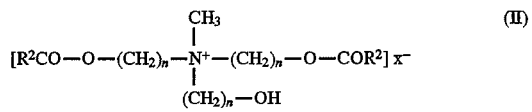

wherein $R^2CO$ is an aliphatic acyl radical containing 12 to 22 carbon atoms and 0, 1, 2 or 3 double bonds, n=2 or 3 and X stands for halide, methosulfate or methophosphate ion are provided which are useful for the production of surface-active agents and for the enhanced recovery of crude oil.

13 Claims, No Drawings

COMPOSITION FOR ENHANCED CRUDE OIL RECOVERY OPERATIONS CONTAINING HYDROCHLORIC ACID OR HYDROFLUORIC ACID, OR MIXTURES THEREOF WITH ESTER QUATERNARY AMMONIUM COMPOUNDS OR/AND ALKYL QUATERNARY AMMONIUM COMPOUNDS

This application is a divisional of Ser. No. 07/943,957, filed Sep. 11, 1992.

BACKGROUND OF THE INVENTION

1. Field of the Invention

This invention relates to detergent compositions containing alkyl and/or alkenyl polyglycosides, ester quats and, optionally, other surfactants and to their use as surface active agents.

2. Description of the Related Art

Alkyl polyglucosides are nonionic surfactants which are synthesized entirely from such renewable raw materials as sugar or starch and fatty alcohol. Apart from their excellent performance properties, they are distinguished by particularly advantageous ecotoxicological compatibility which predestines them for use in a number of fields.

Mixtures of alkyl polyglucosides with other surfactants, more particularly anionic surfactants, are known from a number of publications, of which European patent EP-B-0 070 074 (Procter & Gamble) is cited as representative.

Detergent mixtures containing cationic surfactants in addition to alkyl polyglucosides are also described in a number of publications.

For example, EP-B-0 094 118 (Procter & Gamble) discloses compositions for low-phosphate detergents which, in addition to $C_{12-18}$ alkyl polyglucosides, contain fatty alcohol polyglycol ethers and quaternary ammonium compounds. European patent applications EP-A-0 214 285 and EP-A-0 246 246 (Staley Manuf. Co.) describe liquid disinfectants and light-duty detergents containing alkyl polyglucosides and quaternary ammonium compounds. Finally, liquid detergents containing other anionic and nonionic surfactants in addition to alkyl polyglucosides and quaternary ammonium compounds are known from DE-A-37 02 287 (Colgate).

Although conventional compositions give satisfactory performance results, their biodegradability is inadequate for a number of applications in view of their common component, namely quaternary ammonium compounds (QUATS).

Accordingly, the problem addressed by the present invention was to provide new mixtures based on alkyl polyglucosides and cationic surfactants which would be free from the disadvantages mentioned above.

SUMMARY OF THE INVENTION

One embodiment of the present invention relates to detergent mixtures comprised of: (a) alkyl and/or alkenyl polyglycosides corresponding to formula (I)

$$R^1\text{—O—}[G]_p \qquad (I)$$

in which $R^1$ represents alkyl or alkenyl radicals containing 1 to 22 carbon atoms, [G] is a sugar residue containing 5 or 6 carbon atoms and p is a number of 1 to 10, and (b) ester quats corresponding to formula (II)

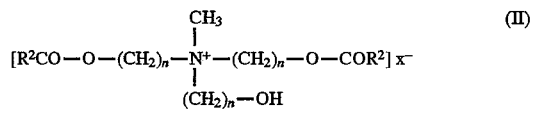

in which $R^2CO$ is an aliphatic acyl radical containing 12 to 22 carbon atoms and 0, 1, 2 or 3 double bonds, n=2 or 3 and X stands for a halide, methosulfate or methophosphate ion. Optionally, the compositions may also contain other anionic, nonionic and/or amphoteric or zwitterionic surfactants.

Another embodiment of the present invention relates to a composition useful in enhanced crude oil recovery operations which is comprised of: (a) a compound of the formula I; (b) aqueous HCl, aqueous HF, or a combination thereof; (c) a quaternary ammonium compound of the formula II, formula III, or a combination thereof wherein the compound of formula III has the general formula $$R_2R_3R_4R_5NX \qquad III$$

wherein $R_2$ is a $C_{6-22}$ alkyl group, and each of $R_3$, $R_4$, and $R_5$ is independently an alkyl group having from about 1 to about 22 carbon atoms and X is a halide ion of a sulfate ion. This composition can be used in enhanced crude oil recovery operations wherein aqueous HCl or HF is pumped down an oil well. When either or both of aqueous HCl or HF is used, the viscosity of the oil in the well increases to the point that it cannot be pumped from the well. It has been unexpectedly discovered that the use of an alkyl polyglucoside permits the oil in the well to be pumped out when a quaternary ammonium compound of formula II and/or III is used to complex $Fe^{+2}$ and/or $Fe^{+3}$ which is normally present in oil wells. Optionally, the composition may also contain a saturated or unsaturated fatty alcohol having from about 8 to about 22 carbon atoms to increase the effectiveness of the alkyl polyglucoside.

DESCRIPTION OF THE PREFERRED EMBODIMENTS

It has surprisingly been found that the detergent mixtures according to the invention not only have excellent performance properties which, in many cases, make them superior to known products, they are also completely biodegradable and toxicologically safe. The invention includes the observation that the alkyl and/or alkenyl polyglycosides support the solubilization of the ester quats in various media and, in particular, largely prevent the formation of poorly soluble salts between the ester quats and any anionic surfactants used.

Alkyl and/or alkenyl polyglycosides are known substances which may be obtained by the relevant methods of preparative organic chemistry. One process for their production is based, for example, on the acid-catalyzed acetalization of glucose with fatty alcohols. European patent application EP-A-0 301 298 is cited as representative of the extensive literature available.

Alkyl and/or alkenyl polyglycosides derived from aldoses or ketoses and—by virtue of its ready availability—above all from glucose are preferred. Accordingly, preferred alkyl polyglycosides are alkyl polyglucosides.

The index p in general formula (I) indicates the degree of polymerization (DP degree), i.e. the distribution of mono- and polyglycosides, and is a number of 1 to 10. Whereas p in a given compound must always have a value of between 1 to 6, the value p for a certain alkyl and/or alkenyl polyglycoside is an analytically determined calculated quantity which will usually be equal to non-integer such as 1.1 or 1.5. Alkyl and/or alkenyl polyglycosides having an average degree of polymerization p of 1.1 to 3.0 are preferred, alkyl and/or alkenyl polyglycosides having a degree of polymerization below 1.7 and, more particularly, between 1.2 and 1.4 being particularly preferred.

The substituent $R^1$ may be derived from saturated and/or unsaturated primary alcohols containing 1 to 22, preferably 8 to 10 or 12 to 18 carbon atoms. Typical examples are methanol, butanol, capric alcohol, 2-ethylhexanol, capryl alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, arachyl alcohol, gadoleyl alcohol, behenyl alcohol and erucyl alcohol and also technical cuts which may contain these alcohols in various quantities. Alkyl and/or alkenyl polyglycosides corresponding to formula (I), in which $R^1$ represents $C_{8-18}$ alkyl radicals, G is a glucose unit and p is a number of 1 to 3, are preferably used.

"Ester quats" are compounds of the formula II and are understood to be technical quaternized difatty acid trialkanolamine ester salts which may be obtained by the relevant methods of preparative organic chemistry. They are normally produced from fatty acids which, in a first step, are esterified with trialkanolamines, such as for example triethanolamine or tripropanolamine. The difatty acid ester formed may then be quaternized in known manner, for example with methyl chloride or dimethyl sulfate. Since they are technical products, the ester quats always contain quaternized monoesters and triesters as secondary products.

Typical examples of the fatty acid components of these compounds are caproic acid, caprylic acid, capric acid, lauric acid, myristic acid, palmitic acid, stearic acid, oleic acid, elaidic acid, petroselic acid, linoleic acid, linolenic acid, arachic acid, gadoleic acid, behenic acid and erucic acid and technical mixtures thereof, for example of the type formed in the hydrogenation of vegetable oils or animal fats. Ester quats based on stearic acid or hydrogenated tallow fatty acid in the form of their chlorides or methosulfates are preferred.

In addition to the alkyl and/or alkenyl polyglycosides, the detergent mixtures according to the invention may contain other anionic, nonionic and amphoteric or zwitterionic surfactants. Examples of anionic surfactants include but are not limited to alkylbenzene sulfonates, alkanesulfonates, olefin sulfonates, alkyl ether sulfonates, glycerol ether sulfonates, α-methyl ester sulfonates, sulfofatty acids, alkyl sulfates, fatty alcohol ether sulfates, (normal-range or narrow-range types), glycerol ether sulfates, hydroxy mixed ether sulfates, monoglyceride (ether) sulfates, fatty acid amide (ether) sulfates, sulfosuccinates, sulfosuccinamates, sulfotriglycerides, ether carboxylic acids, alkyl polyglucoside sulfates and/or alkyl (ether) phosphates. Examples of nonionic surfactants include but are not limited to fatty alcohol ethoxylates (normal-range and narrow-range types), polyol fatty acid esters, sorbitan esters and/or polysorbates. Examples of amphoteric or zwitterionic surfactants include but are not limited to alkyl amidobetaines, aminopropionates, aminoglycinates, imidazolinium betaines and/or sulfobetaines.

The ratio by weight of alkyl and/or alkenyl polyglycosides to ester quats may be 5:95 to 95:5, preferably 10:90 to 90:10 and, more preferably, 30:70 to 70:30. The percentage content of other surfactants in the detergent mixtures may be from 1 to 90% by weight, preferably from 10 to 80% by weight and, more preferably, from 50 to 70% by weight, based on the mixture.

To produce the detergent mixtures according to the invention, the components merely have to be mixed, optionally with heating to 30° to 40° C., and if necessary homogenized. To this end, it is possible to start out from concentrates diluted with water to an in-use concentration of 1 to 50% by weight and preferably 15 to 30% by weight or to use dilute aqueous starting materials. In either case, the operation involved is purely mechanical; no chemical reaction takes place.

Other embodiments of the present invention include: (1) Powder-form universal detergents containing 10 to 30% by weight—based on the detergent—of a mixture of alkyl and/or alkenyl polyglycosides and ester quats and, optionally, other surfactants and typical auxiliaries and additives; (2) Liquid universal detergents containing 10 to 70% by weight—based on the detergent—of a mixture of alkyl and/or alkenyl polyglycosides and ester quats and, optionally, other surfactants and typical auxiliaries and additives; (3) Liquid light-duty detergents containing 10 to 50% by weight—based on the detergent—of a mixture of alkyl and/or alkenyl polyglycosides and ester quats and, optionally, other surfactants and typical auxiliaries and additives; (4) Liquid cleaning and disinfecting preparations containing 10 to 30% by weight—based on the preparation—of a mixture of alkyl and/or alkenyl polyglycosides and ester quats and, optionally, other surfactants and typical auxiliaries and additives; (5) Hair shampoos containing 10 to 30% by weight—based on the shampoo—of a mixture of alkyl and/or alkenyl polyglycosides and ester quats and, optionally, other surfactants and typical auxiliaries and additives; (6) Hair rinses containing 10 to 30% by weight—based on the hair rinse—of a mixture of alkyl and/or alkenyl polyglycosides and ester quats and, optionally, other surfactants and typical auxiliaries and additives; (7) Foam baths containing 10 to 30% by weight—based on the foam bath—of a mixture of alkyl and/or alkenyl polyglycosides and ester quats and, optionally, other surfactants and typical auxiliaries and additives; (8) Compositions for the enhanced recovery of crude oil from occurrences containing 5% to 90% by weight—based on the weight of the composition—of a mixture of alkyl and/or alkenyl polyglycosides, ester quats and, a quaternary ammonium compound of the formula III, a mixture of ester quats and a quaternary ammonium compound of the formula III.

Detergents based on the detergent mixture according to the invention may contain, for example, builders, salts, bleaches, bleach activators, optical brighteners, redeposition inhibitors, solubilizers, foam inhibitors and enzymes as auxiliaries and additives.

Typical builders are sodium aluminum silicates (zeolites), phosphates, phosphonates, ethylenediamine tetraacetic acid, nitrilotriacetate, citric acid and/or polycarboxylates. Suitable salts or diluents are, for example, sodium sulfate, sodium carbonate or sodium silicate (waterglass). Typical individual examples of other additives are sodium borate, starch, sucrose, polydextrose, TAED, stilbene compounds, methyl cellulose, toluene sulfonate, cumene sulfonate, long-chain soaps, silicones, mixed ethers, lipases and proteases.

Hair shampoos, hair lotions or foam baths based on the detergent mixtures according to the invention may contain, for example, emulsifiers, oil components, fats and waxes, thickeners, superfatting agents, biogenic agents, film formers, fragrances, dyes, pearlescers, preservatives and pH regulators as auxiliaries and additives.

Typical oil components are such substances as paraffin oil, vegetable oils, fatty acid esters, squalene and 2-octyl dodecanol. Suitable fats and waxes are, for example, spermaceti, beeswax, montan wax, paraffin and cetostearyl alcohol. Superfatting agents may be selected from such substances as, for example, polyethoxylated lanolin derivatives, lecithin derivatives and fatty acid alkanolamides, the fatty acid alkanolamides also serving as foam stabilizers. Suitable thickeners are, for example, polysaccharides, more particularly xanthan gum, guar guar, agar agar, alginates and tyloses, carboxymethyl cellulose or hydroxyethyl cellulose, also relatively high molecular weight polyethylene glycol monoesters and diesters of fatty acids, polyacrylates, polyvinyl alcohol and polyvinyl pyrrolidone and electrolytes, such as sodium chloride and ammonium chloride. Biogenic agents are understood to be, for example, vegetable extracts, protein hydrolyzates and vitamin complexes. Typical film formers are, for example, polyvinyl pyrrolidone, vinyl pyrrolidine/vinyl acetate copolymers, polymers of the acrylic acid series, quaternary cellulose derivatives and similar compounds. Suitable preservatives are, for example, formaldehyde solution, p-hydroxybenzoate or sorbic acid. Suitable pearlescers are, for example, glycol distearic acid esters, such as ethylene glycol distearate, and also fatty acid monoglycol esters. The dyes used may be selected from any of the substances which are permitted and suitable for cosmetic purposes, as listed for example in the publication "Kosmetische Färbemittel" of the Farbstoffkommission der Deutschen Forschungsgemeinschaft, published by Verlag Chemie, Weinheim, 1984. The dyes are typically used in concentrations of 0.001 to 0.1% by weight, based on the mixture as a whole.

A preferred composition used in enhanced crude oil recovery operations is comprised of from 2% to 30% by weight of dry HCl. The weight ratio of alkyl polyglucoside to quaternary ammonium compound can vary from 50:1 to 1:5. Up to 10% by weight of optional fatty alcohol can be used. A preferred fatty alcohol is Lorol™ 810 fatty alcohol, a trademark product of Henkel Corp., which is a $C_{8-10}$ fatty alcohol.

The detergent mixtures according to the invention are distinguished by excellent detergency performance, hair and fabric softening properties, antistatic finishing of hair and fibers, improvements in compatibility and high ecotoxicological compatibility.

Accordingly, the present invention also relates to their use for the production of laundry detergents, dishwashing detergents and cleaning preparations, hair-care and personal hygiene products and for the enhanced recovery of crude oil.

The following Examples are intended to illustrate the invention without limiting it in any way.

EXAMPLES

I. Substances used

1. Dehydol® LT7 (a product of Henkel KGaA, Düsseldorf/FRG and Henkel Corp., Ambler, Pa. 19002). Adduct of, on average, 7 mol ethylene oxide (EO) with technical $C_{12/18}$ coconut oil fatty alcohol.
2. Texapon® NSO (a product of Henkel KGaA, Düsseldorf/FRG and Henkel Corp., Ambler, Pa. 19002). $C_{12/14}$ coconut oil fatty alcohol 2EO sulfate sodium salt.
3. Plantaren® APG 600 (a product of Henkel KGaA, Düsseldorf/FRG and Henkel Corp., Ambler, Pa. 19002). $C_{12/14}$ coconut oil alkyl polyglucoside having an average degree of polymerization (DP degree) of 1.3.
4. Plantaren® APG 225 (a product of Henkel KGaA, Düsseldorf/FRG and Henkel Corp., Ambler, Pa. 19002). $C_{8/10}$ alkyl polyglucoside having an average degree of polymerization (DP degree) of 1.6.
5. Dehyquart® AU-36 (a product of Pulcra S.A., Barcelona/Spain). Reaction product of technical $C_{16/18}$ tallow fatty acid triethanolamine mono/diester with dimethyl sulfate.

II. Formulation Examples

EXAMPLE 1

Liquid detergent with softening properties

| | |
|---|---|
| Dehydol® LT 7 | 15% by weight |
| Texapon® NSO | 44% by weight |
| Plantaren® APG-600 | 15% by weight |
| Dehyquart AU-36 | 8% by weight |
| Cumene sulfonate Na salt | 4% by weight |
| Water | ad 100 |

The water-based detergent mixture has excellent washing and softening properties and, in addition, provides the treated fabrics with an antistatic finish.

EXAMPLE 2 Lavatory cleaner

| | |
|---|---|
| Plantaren® APG-225 | 7% by weight |
| Dehyquart® AU-36 | 10% by weight |
| Water | ad 100 |

The water-based detergent mixture shows excellent cleaning and disinfecting properties.

EXAMPLE 3

Universal detergent with softening properties

| | |
|---|---|
| Plantaren® APG-600 | 15% by weight |
| Dehyquart® AU-36 | 4.5% by weight |
| Sodium tripolyphosphate | 45% by weight |
| Sodium carbonate | 20% by weight |
| Sodium silicate | 15% by weight |
| Protease | 0.5% by weight |

The powder mixture has very good cleaning properties. In contrast to typical detergents containing cationic surfactants, soil is not reabsorbed onto the fibers.

EXAMPLE 4

Light-duty detergent with softening properties

| | |
|---|---|
| Plantaren® APG-600 | 16% by weight |
| Dehyquart AU-36 | 4% by weight |
| Water | ad 100 |

The water-based detergent mixture combines the properties of a light-duty detergent with those of a fabric softener.

EXAMPLE 5

Enhanced crude oil recovery formulation

| | |
|---|---|
| Dehyguart® AU-36 | 4% by weight |
| Plantaren® APG-600 (50% by weight) | 25% by weight |
| Aqueous hydrochloric acid (20% by weight) | 71% by weight |

The composition of Example 5 was a clear liquid.

EXAMPLE 6

Enhanced crude oil recovery formulation

| | |
|---|---|
| Aliquat ® 336 (Capryl trimethyl-ammonium chloride) | 2% by weight |
| 17% aq. HCl | 78% by weight |
| Plantaren ® APG-225 (50% by weight) | 20% by weight |

The composition of Example 6 was a clear liquid.

EXAMPLE 7

Enhanced crude oil recovery formulation

| | |
|---|---|
| Aliquat ® 336 (Capryl trimethyl-ammonium chloride) | 2% by weight |
| 17% aq. HCl | 78% by weight |
| APG ® 225 | 20% by weight |
| Lorol ™ 810 | 2% by weight |

The composition of Example 7 was a clear liquid.

What is claimed is:

1. A composition for enhanced crude oil recovery comprised of:

(a) a compound of the formula I

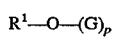

$$R^1\text{—}O\text{—}(G)_p \quad (I)$$

wherein $R^1$ is an alkyl or alkenyl group having from 1 to 22 carbon atoms, (G) is a sugar residue having 5 or 6 carbon atoms and p is a number of 1 to 10;

(b) aqueous HCl or HF or a combination thereof; and (c) at least one quaternary ammonium compound selected from the group consisting of (i) an ester quat of the formula (II)

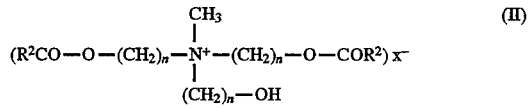

$$\begin{array}{c} CH_3 \\ | \\ (R^2CO\text{—}O\text{—}(CH_2)_n\text{—}N^+\text{—}(CH_2)_n\text{—}O\text{—}COR^2) \, X^- \\ | \\ (CH_2)_n\text{—}OH \end{array} \quad (II)$$

wherein $R^2CO$ is an aliphatic acyl radical containing 12 to 22 carbon atoms and 3 double bonds or less, n=2 or 3, and X is halide, methosulfate or methophosphate ion; and (ii) a quaternary ammonium compound of the formula (III)

$$R_2R_3R_4R_5NX \quad (III)$$

wherein $R_2$ is a $C_{6-22}$ alkyl group, and each of $R_3$, $R_4$, and $R_5$ is independently an alkyl group having from about 1 to about 22 carbon atoms and X is a halide ion or a sulfate ion; wherein the ratio by weight of component (a) to component (c) is from about 50:1 to about 1:5.

2. A composition as claimed in claim 1 further comprising a saturated or unsaturated fatty alcohol having from about 8 to about 22 carbon atoms.

3. The composition of claim 1 wherein from about 2 to about 30% by weight of acid in component (b) is present, based on the weight of the composition.

4. The composition of claim 3 wherein component (b) is aqueous HCl.

5. The composition of claim 3 wherein the composition contains from about 5 to about 90% by weight, based on the weight of the composition, of the total of component (a) plus a component (c).

6. The composition of claim 2 wherein the fatty alcohol is a $C_{8-10}$ fatty alcohol.

7. The composition of claim 1 wherein in component (a) p is a number of from about 1.1 to about 3.0.

8. The composition of claim 7 wherein p is a number of from about 1.2 to about 1.4.

9. The composition of claim 1 wherein in component (a) $R^1$ is a $C_{8-18}$ alkyl group, (G) is glucose, and p is a number of from 1 to about 3.

10. The composition of claim 1 wherein the composition contains from about 5 to about 90% by weight, based on the weight of the composition, of the total of component (a) plus a component (c).

11. The composition of claim 1 wherein component (c) is component (c) (i).

12. The composition of claim 1 wherein component (c) is component (c) (ii).

13. The composition of claim 1 wherein component (c) contains both component (c) (i) and (c) (ii).

* * * * *